(12) United States Patent
Fischer et al.

(10) Patent No.: US 6,355,833 B2
(45) Date of Patent: Mar. 12, 2002

(54) CATALYST COMPRISING AT LEAST ONE NICKEL(0) COMPLEX BASED ON A PHOSPHONITE LIGAND, AND THE PREPARATION OF NITRILES

(75) Inventors: Jakob Fischer, Kirchdorf; Wolfgang Siegel, Limburgerhof, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 22 days.

(21) Appl. No.: 09/782,762

(22) Filed: Feb. 14, 2001

Related U.S. Application Data

(63) Continuation of application No. 09/508,051, filed as application No. PCT/EP98/05733 on Sep. 9, 1998, now Pat. No. 6,242,633.

(30) Foreign Application Priority Data

Sep. 12, 1997 (DE) .......................... 197 40 180

(51) Int. Cl.[7] .............................. C07F 9/6571
(52) U.S. Cl. .................. 562/19; 562/20; 562/23; 562/25; 502/162
(58) Field of Search ............... 562/19, 20, 23, 562/25; 502/162

(56) References Cited

U.S. PATENT DOCUMENTS

| | | | |
|---|---|---|---|
| 3,766,237 A | 10/1973 | Chia et al. | 260/465.3 |
| 5,484,902 A | 1/1996 | Casalnuovo et al. | 536/18.4 |
| 5,512,695 A | 4/1996 | Kreutzer et al. | 558/338 |
| 5,523,453 A | 6/1996 | Breikss | 558/338 |
| 5,600,032 A | 2/1997 | Sato et al. | 568/903 |
| 5,712,403 A | 1/1998 | Sato et al. | 556/19 |
| 5,717,126 A | 2/1998 | Paciello et al. | 558/78 |

FOREIGN PATENT DOCUMENTS

| | | | |
|---|---|---|---|
| DE | 21 61 750 | | 6/1973 |
| DE | 43 21 195 A1 | * | 1/1995 |
| DE | 195 23 335 A1 | * | 1/1996 |
| WO | WO 95/28228 | | 10/1995 |
| WO | WO 95/29153 | | 11/1995 |
| WO | WO 96/11182 | | 4/1996 |
| WO | WO 96/22968 | | 8/1996 |

OTHER PUBLICATIONS

On the Int. Search Report of Priority document: PCT/EP98/05733.*
"Applied Homogenous Catalysis with Organometallic Compounds", vol. 1, VCH Weinheim pp. 465–486, 1996.
Baker et al. "Chelating Diphosphite Complexes of Nickel(0) and Platinum(0); Their Remarkable Stability and Hydrocyanation Activity" J. Chem Soc. Chem Commun. (1991) pp. 803–804.
Casalnuovo et al., "Ligand Electronic Effects in Asymmetric Catalysis: Ehanced Enantioselectivityin the Asymmetric Hydorcyanation of Vinylarenes", J. Am. Chem. Soc., vol. 116, (1994), pp. 9869–9882.
Tolman et al., "Catalytic Hydrocyanation of Olefins by Nickel(0) Phosphite Complexes–Effects of Lewis Acids" Organometallics vol. 3 (1984) pp. 33–38.
Tolman et al., "Homogenous Nickel–Catalyzed Olefin Hydrocyanation" Advances in Catalysis, vol. 33 (1985) pp. 1–47.
Baker et al., "Chiral Aryl Diphosphites: a New Class of Ligands for Hydrocyanation Catalysis" J. Chem Soc. Commun. (1991) pp. 1292–1293.

* cited by examiner

*Primary Examiner*—T. A. Solola
(74) *Attorney, Agent, or Firm*—Keil & Weinkauf

(57) ABSTRACT

A catalyst comprising at least one nickel(O) complex which comprises at least one mono-, bi- or multidentate phosphonite ligand of the formula I

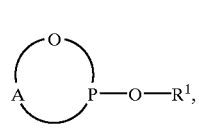

(I)

or salts and mixtures thereof, is prepared as described, and the catalysts are used to prepare mixtures of monoolefinic $C_5$ mononitriles with nonconjugated C═C and C≡N bonds by catalytic hydrocyanation of butadiene or of a 1,3-butadiene-containing hydrocarbon mixture in the presence of a catalyst of this type.

6 Claims, No Drawings

CATALYST COMPRISING AT LEAST ONE NICKEL(0) COMPLEX BASED ON A PHOSPHONITE LIGAND, AND THE PREPARATION OF NITRILES

The present application is a divisional of U.S. patent application Ser. No. 09/508,051, filed Mar. 7,2000, now U.S. Pat. No. 6,242,633, filed as a National Stage Application of PCT/EP 98/05733, Sep. 9, 1998.

DESCRIPTION

The present invention relates to a catalyst which comprises a nickel(0) complex which comprises at least one mono-, bi- or multidentate phosphonite ligand in which the phosphorus and one of the oxygen atoms of the phosphonite group are part of a 5- to 8-membered heterocycle, and to a process for preparing mixtures of monoolefinic $C_5$-mononitriles by catalytic hydrocyanation in the presence of a catalyst of this type.

There is a great demand around the world for α,ω-alkylenediamines which serve as an important starting material for the industrial preparation of polyamides. α,ω-Alkylenediamines such as hexamethylenediamine are obtained almost exclusively by hydrogenation of the corresponding dinitriles. Almost all industrial routes for preparing hexamethylenediamine are therefore essentially variants of the preparation of adiponitrile, of which about 1.0 million tonnes are produced each year around the world.

K. Weissermel, H. -J. Arpe, Industrielle Organische Chemie, 4th edition, VCH Weinheim, pages 266 et seq. describe four routes, which differ in principle, for preparing adiponitrile:

1. reductive amination of adipic acid with ammonia in the liquid or gas phase, with intermediate formation of the diamide;
2. indirect hydrocyanation of 1,3-butadiene via the intermediate 1,4-dichlorobutenes;
3. hydrodimerization of acrylonitrile in an electrochemical process; and
4. direct hydrocyanation of 1,3-butadiene with hydrogen cyanide.

In the last-mentioned process, monoaddition in a first stage results in a mixture of isomeric pentenonitriles which is, in a second stage, isomerized mainly to 3- and 4-pentenonitriles. Subsequently, in a third stage, adiponitrile is formed by anti-Markownikoff addition of hydrogen cyanide onto 4-pentenonitrile. This reaction takes place in the liquid phase in a solvent such as tetrahydrofuran, at a temperature in the range 30–150° C. under atmospheric pressure. The catalysts used for this are nickel complexes with phosphine or phosphite ligands and metal salt promoters. The abovementioned review does not describe phosphonite ligands integrated into a heterocycle for stabilizing the nickel.

"Applied Homogeneous Catalysis with Organometallic Compounds", Volume 1, VCH Weinheim, pages 465 et seq. gives a general description of the addition, with heterogeneous and homogeneous catalysis, of hydrogen cyanide onto olefins. The catalysts used in these cases are in particular based on phosphine, phosphite and phosphinite complexes of nickel and palladium. Adiponitrile is prepared by hydrocyanation of butadiene mainly with the use of nickel(0) phosphite catalysts, in the presence or absence of a Lewis acid as promoter. The reaction can generally be divided into three steps: 1. Synthesis of mononitriles by hydrocyanation of 1,3-butadiene; 2. Isomerization; 3. Synthesis of dinitriles.

In the formation of the monoadduct, a mixture of isomers is obtained and comprises, inter alia, 3-pentenonitrile and 2-methyl-3-butenonitrile.

Customary catalysts for the hydrocyanation of 1,3-butadiene are, in particular, the nickel(0)-phosphite catalysts already mentioned.

C. A. Tolman et al. describe in Organometallics 3 (1984) 33 et seq. the catalytic hydrocyanation of olefins in the presence of nickel(0) phosphite complexes paying particular attention to the effects of Lewis acids on the addition of hydrogen cyanide.

Advances in Catalysis, Volume 33, 1985, Academic Press Inc., page 1 et seq. gives a review-type description of the hydrocyanation of olefins with homogeneous nickel catalysis. The catalysts employed are nickel(0) complexes with phosphine and phosphite ligands.

J. Chem. Soc., Chem. Commun. (1991) 1292 describes chiral aryl diphosphites as ligands for hydrocyanation catalysts. The phosphite group in these ligands is linked by two oxygen atoms to the 3- and 3'-positions of a 2,2'-binaphthyl unit with which they thus form a 7-membered heterocycle. It is also possible in addition for two of these heterocycles to be linked by a 2,2'-binaphthyl unit to give a bidentate chelating ligand.

J. Chem. Soc., Chem. Commun. (1991) 803 et seq. describes chelating diphosphite complexes of nickel(0) and platinum (0) which are analogous thereto but employ a biphenyl unit in place of a 2,2'-binaphthyl unit.

WO 95/28228 describes a process for the hydrocyanation of aliphatic monoolefins which may additionally have a nonconjugated nitrile group or a nonconjugated or conjugated ester group. The nickel(0) catalysts employed in this case likewise comprise bidentate phosphite ligands in which the phosphite groups are parts of aryl-fused heterocycles.

WO 95/29153 describes a process for the hydrocyanation of monoolefins employing catalysts based on zero-valent nickel and monodentate phosphite ligands. The phosphite group in these ligands is in turn, together with two of its oxygen atoms, part of an aryl-fused 7-membered heterocycle. The third oxygen atom of the phosphite group carries a t-butyl-substituted phenyl radical which may also have further substituents.

WO 96/11182 describes a process for the hydrocyanation of aliphatic, monoethylenically unsaturated compounds in which the ethylenic double bond is not conjugated with another unsaturated group or in which the ethylenic double bond is conjugated with an ester group. In this case, a nickel(0) catalyst based on a multidentate phosphite ligand is employed in the presence of a Lewis acid as promoter. The phosphite groups in these multidentate ligands are in turn constituents of aryl-fused heterocycles and may be bridged by aryl-fused groups.

WO 96/22968 describes a process for the hydrocyanation of diolefinic compounds and for the isomerization of the resulting nonconjugated 2-alkyl-3-monoalkenonitriles by reacting an acyclic, aliphatic diolefin with a source of hydrogen cyanide. This reaction takes place in the liquid phase. The hydrocyanation catalysts employed are similar to those described in WO 96/11182.

U.S. Pat. No. 5,512,695 has a disclosure content corresponding to that of WO 95/28228.

Besides the hydrocyanation catalysts described previously and based on mono-, bi- and multidentate phosphite ligands, catalysts based on phosphinite ligands are also known. J. Am. Chem. Soc. 116 (1994) 9869 et seq. and U.S. Pat. No. 5,484,902 describe catalysts for the enantioselective hydrocyanation of aromatic vinyl compounds based on a chiral, nonracemic, bidentate chelating phosphinite ligands. The ligand preferably employed in this case is a phenyl 2,3-bis-O-(3,5-bis(trifluoromethyl)phenyl)phosphino-4,6-O-benzylidene-β-D-glucopyranoside.

U.S. Pat. No. 5,523,453 describes a process for the hydrocyanation of monoolefins which may additionally have a cyano group in the presence of a Lewis acid as promoter and a nickel(0) catalyst. These catalysts have ligands based on chelating phosphinites in which two aryl-substituted phosphinite groups are linked together via their oxygen atom and an aryl-fused alkylene bridge.

None of the abovementioned references describes hydrocyanation catalysts based on phosphonite ligands where the phosphonite group is part of a 5- to 8-membered heterocycle.

U.S. Pat. No. 3,766,237 describes a process for the hydrocyanation of ethylenically unsaturated compounds which may have other functional groups, such as nitriles, in the presence of a nickel catalyst. These nickel catalysts have four ligands of the formula M(X,Y,Z) where X, Y and Z are, independently of one another, a radical R or OR, and R is selected from alkyl and aryl groups having up to 18 carbon atoms. However, only phosphines and phosphites are explicitly mentioned therein and employed in the examples of the hydrocyanation. On the other hand, there is no disclosure of the possibility of employing phosphonites in which the phosphonite group is part of a heterocycle as ligands for nickel(0) hydrocyanation catalysts.

It is an object of the present invention to provide novel catalysts based on zero-valent nickel which show good selectivity and good catalytic activity in the hydrocyanation of 1,3-butadiene-containing hydrocarbon mixtures and in the first and second additions of hydrogen cyanide to prepare adiponitrile.

We have found that this object is achieved by catalysts based on nickel(0) complexes which comprise at least one mono-, bi- or multidentate phosphonite ligand where the phosphonite group is part of a 5- to 8-membered heterocycle.

The present invention thus relates to a catalyst comprising a nickel(0) complex having at least one mono-, bi- or multidentate phosphonite ligand of the formula I

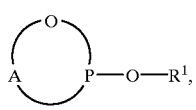

(I)

where
A is, together with the part of the phosphonite group to which it is bonded, a 5- to 8-membered heterocycle which may additionally be fused once, twice or three times to cycloalkyl, aryl and/or hetaryl where the fused groups may in each case have one, two or three substituents selected from alkyl, alkoxy, halogen, nitro, cyano or carboxyl, $R^1$ is alkyl, aryl or hetaryl, each of which may have one, two or three of the following substituents: alkyl, cycloalkyl, aryl, alkoxy, cycloalkyloxy, acyl, aryloxy, halogen, trifluoromethyl, nitro, cyano, carboxyl or $NE^1E^2$, where $E^1$ and $E^2$ may be identical or different and are alkyl, cycloalkyl or aryl, or $R^1$ is a radical of the formula II

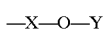

(II)

where
X is a $C_3$–$C_6$-alkylene bridge which may have one, two or three double bonds and/or be fused once, twice or three times with aryl and/or hetaryl, where the aryl or hetaryl groups may have one, two or three of the following substituents: alkyl, cycloalkyl, aryl, alkoxy, cycloalkyloxy, aryloxy, halogen, trifluoromethyl, nitro, cyano, carboxyl or $NE^1E^2$, where $E^1$ and $E^2$ have the abovementioned meanings,
Y is a radical of the formula III.1 or III.2

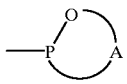

(III.1)

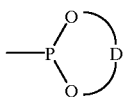

(III.2)

where
D can have the meanings stated previously for A, or salts and mixtures thereof.

The term alkyl comprises for the purpose of the present invention straight-chain and branched alkyl groups. These are preferably straight-chain or branched $C_1$–$C_8$-alkyl, more preferably $C_1$–$C_6$-alkyl and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

The cycloalkyl group is preferably a $C_5$–$C_7$-cycloalkyl group such as cyclopentyl, cyclohexyl or cycloheptyl.

If the cycloalkyl group is substituted, it preferably has 1, 2, 3, 4 or 5, in particular 1, 2 or 3, substituents selected from alkyl, alkoxy or halogen.

Aryl is preferably phenyl, tolyl, xylyl, mesityl, naphthyl, anthracenyl, phenanthrenyl, naphthacenyl and, in particular phenyl or naphthyl.

Substituted aryl radicals preferably have 1, 2, 3, 4 or 5, in particular, 1, 2 or 3, substituents selected from alkyl, alkoxy or halogen.

Hetaryl is preferably pyridyl, quinolinyl, acridinyl, pyridazinyl, pyrimidinyl or pyrazinyl.

Substituted hetaryl radicals preferably have 1, 2 or 3 substituents selected from alkyl, alkoxy or halogen.

The above statements on alkyl, cycloalkyl and aryl radicals apply correspondingly to alkoxy, cycloalkyloxy and aryloxy radicals. The radicals $NE^1E^2$ are preferably N,N-dimethyl, N,N-diethyl, N,N-dipropyl, N,N-diisopropyl, N,N-di-n-butyl, N,N-di-t-butyl, N,N-dicyclohexyl or N,N-diphenyl.

Halogen is fluorine, chlorine, bromine and iodine, preferably fluorine, chlorine and bromine.

In a preferred embodiment of the invention, the catalysts comprise at least one phosphonite ligand of the formula I where A is, together with the part of the phosphonite group to which it is bonded, a 5- or 6-membered heterocycle which may be fused once or twice to aryl and/or hetaryl, where the fused groups may have one, two or three of the abovementioned substituents.

The radical A is then, for example, a 2,2'-biphenylylene, 2,2-binaphthylylene or 2,3-xylylene radical which may have 1, 2 or 3 substituents selected from alkyl, alkoxy or halogen. In this case, alkyl is preferably $C_1$–$C_4$-alkyl and, in particular, t-butyl. Alkoxy is preferably $C_1$–$C_4$-alkoxy and, in particular, methoxy. Halogen is, in particular, fluorine, chlorine or bromine.

A is, in particular, a radical of the formula IV.1, IV.2 or IV.3:

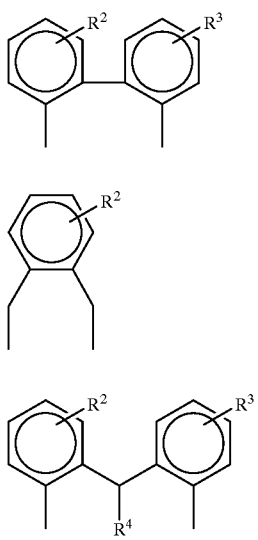

where
$R^2$ and $R^3$ are, independently of one another, hydrogen, alkyl, alkoxy, halogen, trifluoromethyl, nitro or cyano, and
$R^4$ is hydrogen, alkyl, preferably methyl, or aryl, preferably phenyl, which may be substituted by alkyl, alkoxy, halogen, trifluoromethyl, nitro or cyano.

The above statements on preferred radicals A apply correspondingly to radicals D.

In another preferred embodiment, the novel catalysts comprise at least one phosphonite ligand of the formula I where
$R^1$ is phenyl or naphthyl, which may have one, two or three of the following substituents: alkyl, alkoxy, halogen, nitro, cyano, carboxyl or $NE^1E^2$, where $E^1$ and $E^2$ have the abovementioned meanings, or
$R^1$ is a radical of the formula II where
X is a $C_4$–$C_5$-alkylene bridge which may have one or two double bonds and/or be fused once or twice to aryl and/or hetaryl, where the aryl or hetaryl groups may have one, two or three of the following substituents: alkyl, cycloalkyl, aryl, alkoxy, cycloalkyloxy, aryloxy, halogen, nitro, cyano, carboxyl or $NE^1E^2$, where $E^1$ and $E^2$ have the abovementioned meanings, and
Y is a radical of the formula III.1 or III.2, where D is a radical of the formula IV.1, IV.2 or IV.3.

If $R^1$ is phenyl or naphthyl, this preferably has 1, 2 or 3 substituents selected from $C_1$–$C_4$-alkyl, $C_1$–$C_4$-alkoxy or halogen. The substituents are particularly selected from t-butyl, methoxy, trifluoromethyl, fluorine, chlorine and bromine.

If $R^1$ is a radical of the formula II where X is a $C_4$–$C_5$-alkylene bridge, this is preferably fused once or twice to phenyl and/or naphthyl, where the phenyl or naphthyl groups may have 1, 2 or 3 of the following substituents: t-butyl, methoxy, fluorine, chlorine or bromine.

Preferably residue $R^1$ of formula I is a radical of the formula II where X is a residue of the formulae X.1 to X.5

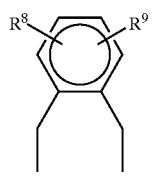

(X.1)

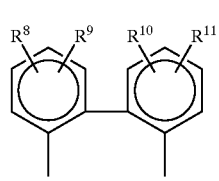

(X.2)

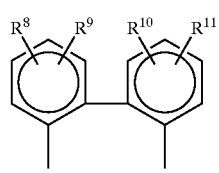

(X.3)

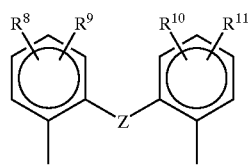

(X.4)

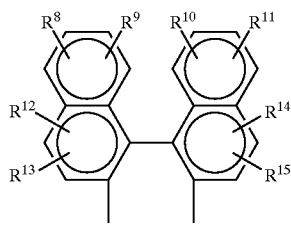

(X.5)

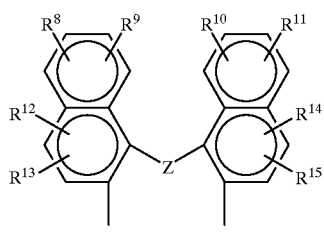

wherein

Z is O, S, $NR^{16}$ or $CHR^{17}$, wherein
$R^{16}$ is alkyl, cycloalkyl or aryl, and
$R^{17}$ is hydrogen, alkyl, cycloalkyl or aryl, where the aryl substituent may have one, two or three of the following substituents: alkyl, alkoxy, halogen, trifluormethyl, nitro, alkoxycarbonyl or cyano,
$R^8$, $R^9$, $R^{10}$, $R^{11}$, $R^{12}$, $R^{13}$, $R^{14}$ and $R^{15}$ are, independently of one another, hydrogen, alkyl, alkoxy, halogen, trifluormethyl, nitro, alkoxycarbonyl or cyano.

Preferably X is a residue of the formula X.1 wherein $R^8$ and $R^9$ are hydrogen.

Preferably X is a residue of the formula X.2a

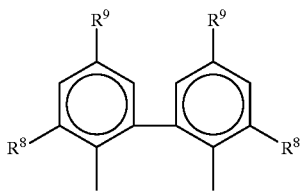
(X.2a)

wherein

R$^8$ is hydrogen or C$_1$–C$_4$-alkyl, particularly methyl, isopropyl or t-butyl, R$^9$ is hydrogen, C$_1$–C$_4$-alkyl, particularly methyl, isopropyl, t-butyl, C$_1$–C$_4$-alkoxy, particularly methoxy, fluorine, chlorine or trifluormethyl.

Preferably X is a residue of the formula X.3a

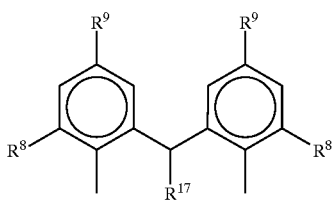
(X.3a)

wherein

R$^8$ and R$^9$ have the meanings mentioned above for formula X.2a,

R$^{17}$ is hydrogen, C$_1$–C$_4$-alkyl, particularly methyl or ethyl, phenyl, p-(C$_1$–C$_4$-alkoxy)phenyl, particularly p-methoxy phenyl, p-fluorophenyl, p-chlorophenyl or p-(trifluoromethyl)phenyl.

Preferably X is a residue of the formula X.4, wherein R$^8$, R$^9$, R$^{10}$, R$^{11}$, R$^{12}$, R$^{13}$, R$^{14}$ and R$^{15}$ are hydrogen.

Preferably X is a residue of the formula X.4, wherein R$^8$, R$^9$, R$^{10}$, R$^{11}$, R$^{13}$ and R$^{15}$ are hydrogen and R$^{12}$ and R$^{14}$ are, independently of one another, alkoxycarbonyl, particularly methoxy carbonyl, ethoxy carbonyl, n-propyloxy carbonyl or isopropyloxy carbonyl. R$^{12}$ and R$^{14}$ are especially in the ortho-position with respect to the phosphonite group.

Preferably X is a residue of the formula X.5 wherein R$^8$, R$^9$, R$^{10}$, R$^{11}$, R$^{12}$, R$^{13}$, R$^{14}$ and R$^{15}$ are hydrogen, and Z is CR$^{17}$, wherein R$^{17}$ has the abovementioned meanings.

Preferably X is a residue of the formula X.5 wherein R$^8$, R$^9$, R$^{10}$, R$^{11}$, R$^{13}$ and R$^{15}$ are hydrogen, Z is CR$^{17}$, and R$^{12}$ and R$^{14}$ are, independently of one another, alkoxy carbonyl, particularly methoxy carbonyl, ethoxy carbonyl, n-propyloxy carbonyl or isopropyloxy carbonyl. R$^{12}$ and R$^{14}$ are especially in the ortho-position with respect to the phosphonite group.

In a suitable embodiment, the phosphonite ligands of the formula I are selected from ligands of the formulae Ia to Ih

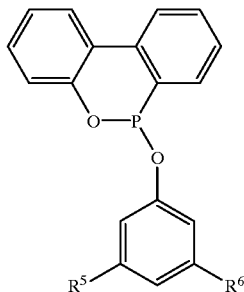
(Ia)

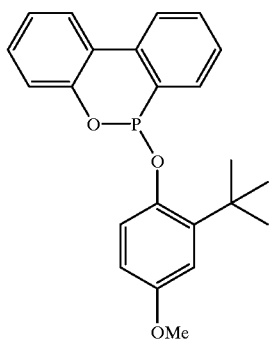
(Ib)

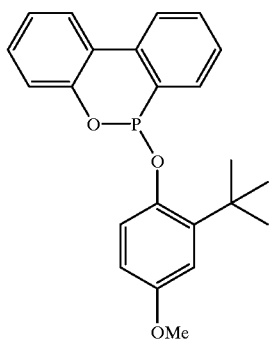
(Ic)

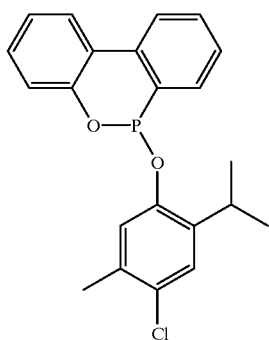
(Id)

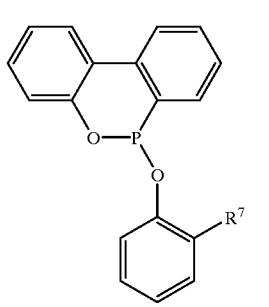
(Ie)

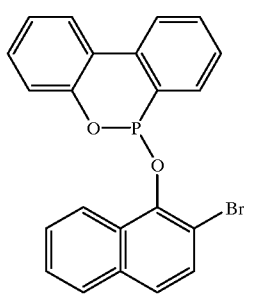

-continued

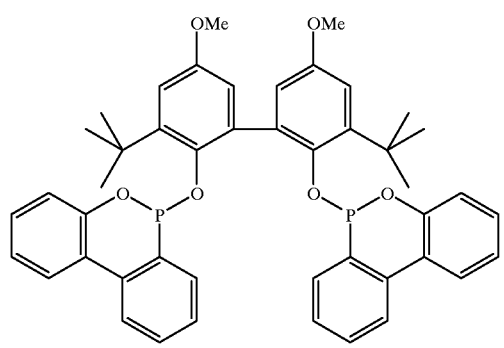

(If)

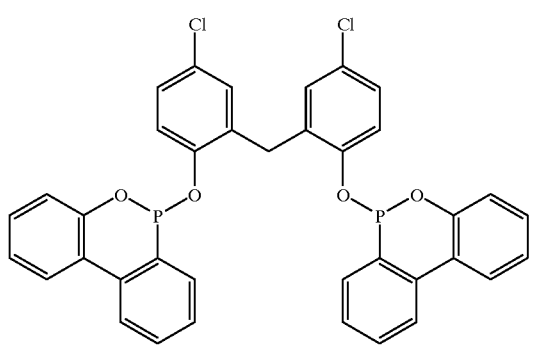

(Ig)

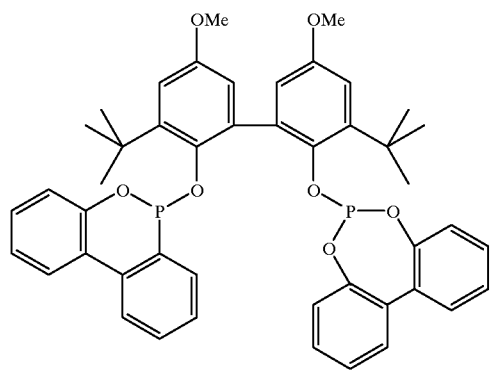

(Ih)

where
R⁵ and R⁶ are, independently of one another, hydrogen or trifluoromethyl,
R⁷ is fluorine or trifluoromethyl.

The novel catalysts may have one or more of the phosphonite ligands of the formula I. In addition to the previously described ligands of the formula I, they may also have at least one other ligand which is selected from halides, amines, carboxylates, acetylacetonate, aryl- or alkylsulfonates, hydride, CO, olefins, dienes, cycloolefins, nitrites, N-containing heterocycles, aromatic and heteroaromatic compounds, ethers, PF₃ and mono-, bi- and multidentate phosphine, phosphinite, phosphonite and phosphite ligands. These other ligands may likewise be mono-, bi- or multidentate and be coordinated to zero-valent nickel. Other suitable phosphorus-containing ligands are, for example, the phosphine, phosphinite and phosphite ligands described previously as prior art.

The phosphonite ligands of the formula I employed according to the invention can be prepared, for example, by reacting a hydroxyl-containing compound of the formula V with a phosphorus trihalide, preferably PCl₃, to give a compound of the formula VI and then reacting the latter with a hyroxyl-containing compound of the formula HOR¹ as shown in the following diagram

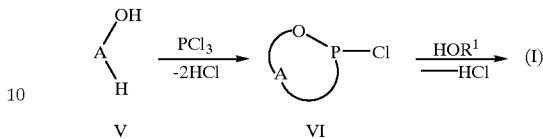

where A and R¹ have the abovementioned meanings. A process of this type is described in Phosphorus and Sulfur, 1987, Vol. 31, page 71 et seq. for synthesizing 6H-dibenz [c,e][1,2]oxaphosphorine ring systems.

Examples of suitable alcohols of the formula V are 2-biphenylol, 2-binaphthylol etc.

Examples of suitable alcohols of the formula HOR¹ are 2-tert-butyl-4-methylphenol, 2-tert-butylphenol, 4-tert-butylphenol, 2,6-di-tert-butyl-4-methylphenol, 2,4-di-tert-butylphenol, 2,6-di-tert-butylphenol, 2,4-dimethylphenol, 2,5-dimethylphenol, 2,6-dimethylphenol, 3,4-dimethylphenol, 3,5-dimethylphenol, 2-ethylphenol, 3-ethylphenol, 4-ethylphenol, 5-isopropyl-2-methylphenol, m-cresol, o-cresol, p-cresol, 1-naphthol, 2-naphthol, phenol, 1-bromo-2-naphthol, 3-bromophenol, 5-chloroquinolin-8-ol, 4-chloro-3,5-dimethylphenol, 2-chloro-5-methylphenol, 4-chloro-3-methylphenol, 2-chloro-6-nitrophenol, 2-chlorophenol, 3-chlorophenol, 4-chlorophenol, 4-chlororesorcinol, 2,3-dichlorophenol, 2,4-dichlorophenol, 2,5-dichlorophenol, 2,6-dichlorophenol, 3,4-dichlorophenol, 2-fluorophenol, 3-fluorophenol, 4-fluorophenol, 3-methyl-4-nitrophenol, 2-nitroanisole, 4-nitrocatechol, 2-nitrophenol, 3-nitrophenol, 2-methoxymethylphenol, 2-methoxy-4-methylphenol, 2-methoxyphenol, 3-methoxyphenol, 4-methoxyphenol. Preferred alcohols of the formula HOR¹ are 2,6-di-tert-butyl-4-methylphenol, 2,4-di-tert-butylphenol, 2,6-di-tert-butylphenol, phenol, 2-fluorophenol, 3-fluorophenol, 4-fluorophenol, 4-nitrocatechol, 2-methoxy-4-methylphenol, 2-trifluoromethylphenol, 3,5-bis(trifluoromethyl)phenol, 4-cyanophenol, etc.

Bidentate chelating ligands can be prepared by employing a compound of the formula HOR¹ where the radical R¹ has another hydroxyl group. Examples thereof are biphenyl-2,2'-diol and binaphthyl-2,2'-diol. Further suitable diols are mentioned in U.S. Pat. No. 5,312,996, column 19, which is incorporated herein by reference. If at least 2 mole equivalents of compound VI are employed for the reaction, a pure bidentate phosphonite ligand of the formula I is obtained. However, bidentate ligands of the formula I which have a phosphonite group and a phosphite group can also be prepared by reacting a compound of the formula VI with a compound of the formula HOR¹ which has two hydroxyl groups to give a monocondensate, and then reacting the latter with a compound of the formula VII

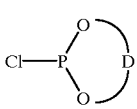

VII where D may have the meanings mentioned above for A, to give a mixed ligand of the formula I.

The compounds of the formula VI can be isolated if required and subjected to purification, for example by distillation. Reaction of the compound of the formula V to give a compound of the formula VI generally takes place at an elevated temperature in a range from about 40 to about 200° C., it also being possible to carry out the reaction while increasing the temperature gradually. In addition, a Lewis acid such as zinc chloride or aluminum chloride can be added as catalyst at the start of the reaction or after a certain reaction time. Further reaction of the compounds of the formula VI to give the phosphonite ligands of the formula I employed according to the invention generally takes place in the presence of a base, eg. an aliphatic amine such as diethylamine, dipropylamine, dibutylamine, trimethylamine, tripropylamine and, preferably, triethylamine or pyridine.

The phosphonite ligands of the formula I employed according to the invention are advantageously prepared without using organomagnesium or -lithium compounds. The simple reaction sequence means that it is possible to vary the ligands widely. The preparation thus takes place efficiently and economically from easily obtainable precursors.

The novel catalysts can be prepared by reacting at least one phosphonite ligand of the formula I with nickel or a nickel compound in the presence of a reducing agent or with a nickel complex in an inert solvent. Suitable nickel compounds in this context are, for example, compounds in which the transition metal assumes an oxidation state above 0 and which are reduced in situ on reaction with the phosphonite ligands of the formula I, where appropriate in the presence of a suitable reducing agent. These include, for example, the halides, preferably the chlorides, and the acetates of the abovementioned transition metals. $NiCl_2$ is preferably employed. Examples of suitable reducing agents are metals, preferably alkali metals such as Na and K, aluminum, zinc and trialkylaluminum compounds.

If the phosphonite-nickel(0) complexes are prepared using complex compounds of the transition metal, the transition metal is preferably present in the latter in the zero valent state. The complexes preferably employed for the preparation are those with ligands corresponding to the abovementioned additional ligands in the novel complexes. In this case, the preparation takes place by partial or complete ligand exchange with the phosphonite ligands of the formula I described previously.

In a suitable embodiment of the novel process, the nickel complex is bis(1,5-cyclooctadiene)nickel(0).

Suitable inert solvents for preparing the nickel(0) complexes are, for example, aromatic compounds such as benzene, toluene, ethylbenzene, chlorobenzene, ethers, preferably diethyl ether and tetrahydrofuran, or haloalkanes, for example dichloromethane, chloroform, dichloroethane and trichloroethane. The temperature is in the range from −70° C. to 150° C., preferably from 0° C. to 100° C., particularly preferably at about room temperature.

If elemental nickel is employed for preparing the phosphonite-nickel(0) complexes, it is preferably in the form of a powder. The nickel and the phosphonite ligand are preferably reacted in a product of the hydrocyanation reaction as solvent, eg. in a mixture of monoolefinic $C_5$-mononitriles or, preferably in 3-pentenenitrile. It is also possible, where appropriate, for the ligand to be employed as solvent. The temperature is in the range from about 0 to 150° C., preferably 60 to 100° C.

The invention further relates to a process for preparing mixtures of monoolefinic $C_5$-mononitriles with nonconjugated C=C and C≡N bonds by catalytic hydrocyanation of a 1,3-butadiene-containing hydrocarbon mixture, which comprises carrying out the hydrocyanation in the presence of at least one of the novel catalysts described previously.

It is preferable to employ in the novel process for preparing monoolefinic $C_5$-mononitriles a hydrocarbon mixture which has a 1,3-butadiene content of at least 10% by volume, preferably at least 25% by volume, in particular at least 40% by volume.

It is possible to employ pure butadiene or 1,3-butadiene-containing hydrocarbon mixtures for preparing mixtures of monoolefinic $C_5$-mononitriles which comprise, for example, 3-pentenenitrile and 2-methyl-3-butenenitrile and which are suitable as intermediates for further processing to adiponitrile.

1,3-Butadiene-containing hydrocarbon mixtures are obtainable on the industrial scale. Thus, for example, petroleum processing by naphtha steam cracking results in a hydrocarbon mixture which is referred to as the $C_4$ cut and has a high total olefin content, about 40% being 1,3-butadiene and the remainder being monoolefins and polyunsaturated hydrocarbons plus alkanes. These streams always also contain small amounts, in general up to 5%, of alkanes, 1,2-dienes and vinylacetylene.

Pure 1,3-butadiene can be isolated, for example, by extractive distillation from industrially obtainable hydrocarbon mixtures.

$C_4$ Cuts are essentially freed where appropriate of alkynes such as propyne or butyne, of 1,2-dienes such as propadiene, and of alkenynes such as vinylacetylene. Otherwise, the resulting products in some circumstances have a C=C double bond conjugated with the C≡N bond. It is disclosed in Applied Homogeneous Catalysis with Organometallic Compounds, Vol. 1, VCH Weinheim, page 479, that the conjugated 2-pentenenitrile produced in the isomerization of 2-methyl-3-butenenitrile and 3-pentenenitrile acts as inhibitor of the second addition of hydrogen cyanide to give adiponitrile. It has been found that the abovementioned conjugated nitriles obtained in the hydrocyanation of a non-pretreated $C_4$ cut also act as catalyst poisons for the first step in the preparation of adipic acid, the monoaddition of hydrogen cyanide.

Those components which afford catalyst poisons in the catalytic hydrocyanation, especially alkanes, 1,2-dienes and mixtures thereof, are therefore partly or completely removed, where appropriate, from the hydrocarbon mixture. To remove these components, the $C_4$ cut is subjected to a partial catalytic hydrogenation before the addition of hydrogen cyanide. This partial hydrogenation takes place in the presence of a hydrogenation catalyst which is able to hydrogenate alkanes and 1,2-dienes selectively in the presence of other dienes and monoolefins.

Suitable heterogeneous catalyst systems generally comprise a transition metal compound on an inert carrier. Suitable inert carriers are the oxides customary for this purpose, especially silicon and aluminum oxides, aluminosilicates, zeolites, carbides, nitrides etc. and mixtures thereof. The carriers preferably used are $Al_2O_3$, $SiO_2$ and mixtures thereof. The heterogeneous catalysts used are, in particular, those described in U.S. Pat. No. 4,587,369, U.S. Pat. No. 4,704,492 and U.S. Pat. No. 4,493,906, which are incorporated herein by reference. Further suitable Cu-based catalyst systems are marketed by Dow Chemical as KLP catalyst.

The addition of hydrogen cyanide onto 1,3-butadiene or a 1,3-butadiene-containing hydrocarbon mixture, eg. a pretreated, partially hydrogenated $C_4$ cut, can take place continuously, semicontinuously or batchwise.

In a suitable variant of the novel process, the addition of hydrogen cyanide takes place continuously. Suitable reactors for the continuous reaction are known to the skilled worker and are described, for example, in Ullmanns Enzyklopädie der technischen Chemie, Vol. 1, 3rd edition, 1951, pages 743 et seq. A cascade of stirred vessels or a tubular reactor is preferably used for the continuous variant of the novel process.

In a preferred variant of the novel process, the addition of hydrogen cyanide onto 1,3-butadiene or a 1,3-butadiene-containing hydrocarbon mixture takes place semicontinuously.

The semicontinuous process comprises:
a) charging a reactor with the hydrocarbon mixture, where appropriate part of the hydrogen cyanide and a novel hydrocyanation catalyst, which may have been generated in situ, and, where appropriate, a solvent,
b) reacting the mixture at elevated temperature under elevated pressure, with, in the semicontinuous procedure, hydrogen cyanide being fed in as it is consumed,
c) completing the conversion by subsequent reaction followed by workup.

Suitable pressure-resistant reactors are known to the skilled worker and are described, for example, in Ullmanns Enzyklopädie der technischen Chemie, Vol. 1, 3rd edition, 1951, pages 769 et seq. An autoclave is generally used for the novel process and may, if required, be equipped with a stirring device and an inner lining. The following should preferably be noted for the above steps:

Step a):
The pressure-resistant reactor is charged before starting the reaction with the partially hydrogenated $C_4$ cut, hydrogen cyanide, a hydrocyanation catalyst and, where appropriate, a solvent. Suitable solvents in this case are those mentioned previously for the preparation of the novel catalysts, preferably aromatic hydrocarbons such as toluene and xylene, or tetrahydrofuran.

Step b):
The mixture is generally reacted at elevated temperature under elevated pressure. This reaction is generally carried out at about 0 to 200° C., preferably about 50 to 150° C., more preferably 70 to 120° C. The pressure is generally in a range of about 0,1 to 200 bar, preferably 1 to 200 bar, more preferably about 1 to 100 bar, in particular 1 to 50 bar, particularly preferably 1 to 15 bar. During this reaction, hydrogen cyanide is fed in as it is consumed, with the pressure in the autoclave remaining essentially constant. The reaction takes about 30 minutes to 5 hours.

Step c):
It is possible to complete the reaction by subsequent reaction for from 0 minutes to about 5 hours, preferably about 1 hour to 3.5 hours, during which no further hydrogen cyanide is fed into the autoclave. The temperature during this is kept essentially constant at the reaction temperature previously set. Workup takes place by conventional processes and comprises removing the unreacted 1,3-butadiene and unreacted hydrogen cyanide, for example by washing or extraction, and workup by distillation of the remaining reaction mixture to remove the required products and recover the still active catalyst.

In another suitable variant of the novel process, the addition of hydrogen cyanide onto the 1,3-butadiene-containing hydrocarbon mixture takes place batchwise. The reaction conditions in this case are essentially those described for the semicontinuous process, with the hydrogen cyanide being entirely present from the outset, so there is no additional feeding in taking place in step b).

In general, the preparation of adiponitrile from a butadiene-containing mixture by addition of 2 mole equivalents of hydrogen cyanide can be divided into three steps:

1. Preparation of $C_5$-monoolefin mixtures with nitrile functionality.
2. Isomerization of the 2-methyl-3-butenonitrile present in these mixtures to 3-pentenonitrile and isomerization of the 3-pentenonitrile formed in this way and already present in the mixtures from step 1 to various n-pentenonitriles. The aim here is form the maximum amount of 3-pentenonitrile and 4-pentenonitrile and the minimum amount of conjugated 2-pentenonitrile and 2-methyl-2-butenonitrile, which may act as catalyst poisons.
3. Preparation of adiponitrile by addition of hydrogen cyanide onto 3-pentenonitrile which was formed in step 2 and is previously isomerized in situ to 4-pentenonitrile. Byproducts occurring in this case are, for example, 2-methyl-glutaronitrile from Markownikoff addition of hydrogen cyanide onto 4-pentenonitrile or anti-Markownikoff addition of hydrogen cyanide onto 3-pentenonitrile, and ethylsuccinonitrile from Markownikoff addition of hydrogen cyanide onto 3-pentenonitrile.

The novel catalysts based on phosphonite ligands are also suitable and advantageous for the positional and double-bond isomerization in step 2 and/or the second addition of hydrogen cyanide in step 3.

In a suitable embodiment of the novel process, the ratio of the amounts of 3-pentenonitrile and 2-methyl-3-butenonitrile obtained in the monoaddition of hydrogen cyanide onto the 1,3-butadiene-containing hydrocarbon mixture is at least 1.9:1, preferably at least 2.1:1.

It is advantageous that the catalysts employed according to the invention not only show high selectivity with regard to the monoaddition products obtained on hydrocyanation of 1,3-butadiene-containing hydrocarbon mixtures, but can also be mixed with an excess of hydrogen cyanide in the hydrocyanation with negligible separation out of inactive nickel(II) compounds such as nickel(II) cyanide. In contrast to known hydrocyanation catalysts based on noncomplex phosphine and phosphite ligands, the catalysts of the formula I are thus suitable not only for continuous hydrocyanation processes in which an excess of hydrogen cyanide in the reaction mixture can generally be effectively avoided, but also for semicontinuous processes and batch processes in which a large excess of hydrogen cyanide is generally present. Thus, the catalysts employed according to the invention, and the hydrocyanation processes based on them, generally show higher catalyst recycling rates and longer catalyst useful lives than known processes. This is advantageous not only economically but also from the ecological viewpoint because the nickel cyanide formed from the active catalyst with hydrogen cyanide is highly poisonous and must be reprocessed or disposed of at high cost.

Besides the hydrocyanation of 1,3-butadiene-containing hydrocarbon mixtures, the catalysts of the formula I are generally suitable for all conventional hydrocyanation processes. Mention may be made in this connection in particular of the hydrocyanation of nonactivated olefins, eg. of styrene and 3-pentenonitrile.

The catalysts described above and comprising chiral phosphonite ligands of the formula I are suitable for enantioselective hydrocyanation.

The invention is explained in detail by the following, non-limiting examples.

EXAMPLES

A) Preparation of the ligands Ia to Ig

Example 1

Preparation of ligand Ia 206 g (1.5 mol) of phosphorus trichloride and 204 g (1.2 mol) of 2-biphenylol are slowly heated with stirring under an argon atmosphere to 50° C. and further to 140° C. over the course of 8 hours. There is vigorous evolution of hydrogen chloride, and the solution becomes yellow. After cooling to 120° C., a catalytic amount of zinc chloride (1.2 g; 17 mmol) is added, and the mixture is heated at 140° C. for 24 hours. In the subsequent distillation, the product 6-chloro-(6H)-dibenz[c,e][1,2]oxaphosphorine distils at 132° C. (0.2 mbar). Yield: 194.8 g (69%) of white crystals; $^{31}$P-NMR spectrum: δ (ppm) 134.5.

0.1 mol of this product is introduced together with 0.1 mol of phenol into 50 ml of toluene under an argon atmosphere. At room temperature, 0.1 mol of triethylamine (dried over KOH) is added dropwise. The mixture is then stirred at 40° C. for one hour. The resulting triethylammonium chloride is filtered off, and the volatile constituents are removed under high vacuum. A transparent oily product (crude yield 100%) remains. The ligand can be purified further by washing with n-hexane or recrystallization.

$^{31}$P-NMR spectrum: δ (ppm) 127.4; purity of crude product: 97%

$^1$H-NMR: corresponds to the spectrum expected for ligand Ia

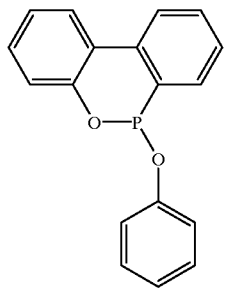

(Ia)

Example 2

Preparation of ligand Ib

Ligand Ib is prepared by a method similar to that indicated in Example 1.

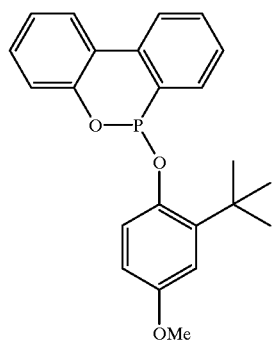

(Ib)

$^{31}$P-NMR spectrum: δ (ppm) 125.3

$^1$H-NMR consistent with the proposed structure

Purity of crude product: >90%

Example 3

Preparation of Ligand Ic

Ligand Ic is prepared by a method similar to that indicated in Example 1.

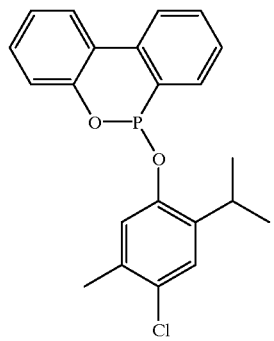

(Ic)

$^{31}$P-NMR spectrum: δ (ppm) 128.02

$^1$H-NMR spectrum: consistent with the proposed structure $^{13}$C-NMR spectrum: consistent with the proposed structure Purity of crude product: >95%

Example 4

Preparation of ligand Id

Ligand Id is prepared by a method similar to that indicated in Example 1.

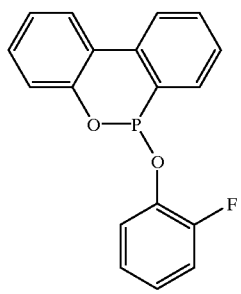

(Id)

$^{31}$P-NMR spectrum: δ (ppm) 131.44

$^{1}$H-NMR spectrum: consistent with the proposed structure $^{13}$C-NMR spectrum: consistent with the proposed structure Purity of crude product: >87%

Example 5

Preparation of ligand Ie

Ligand Ie is prepared by a method similar to that indicated in Example 1.

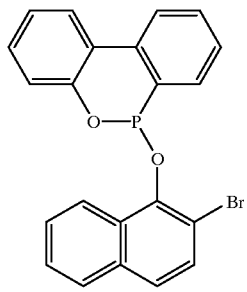

(Ie)

31P-NMR spectrum: δ (ppm) 131.41

$^{1}$H-NMR spectrum: consistent with the proposed structure $^{13}$C-NMR spectrum: consistent with the proposed structure Purity of crude product: >88%

Example 6

Preparation of ligand If

6-Chloro-(6H)-dibenz[c,e][1,2]oxaphosphorine is prepared by a method similar to that indicated in Example 1.

40 g (0.177 mol) of 6-chloro-(6H)-dibenz[c,e][1,2]-oxaphosphorine are introduced together with 31.7 g (0.088 mol) of 5,5'-dimethoxy-3,3'-di-t-butyl-2,2'-biphenol into 400 ml of toluene under argon. At room temperature, 20.24 g (0.2 mol) of triethylamine (dried over KOH) are added dropwise. The mixture is then stirred at 90° C. for 120 minutes. The resulting triethylammonium chloride is filtered off, and the residue on the filter is washed with tetrahydrofuran for completion of the yield. The volatile constituents are removed from the combined organic phases under high vacuum. Ligand If is obtained as crude product in a yield of 100%. The white/yellow solid is washed first with n-hexane and then with diethyl ether.

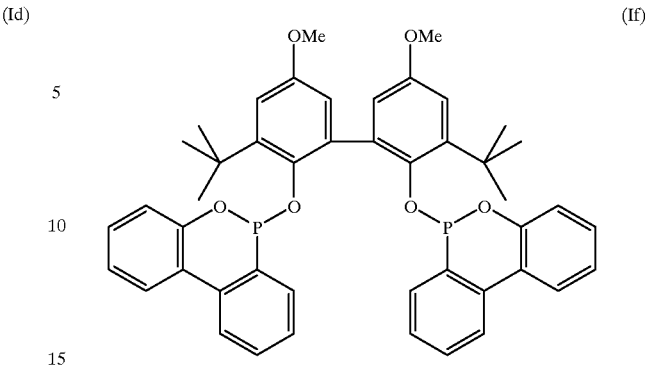

(If)

$^{31}$P-NMR spectrum: δ (ppm) 128.14

Example 7

Preparation of ligand Ig

Ligand Ig is prepared by a method similar to that indicated in Example 6. The resulting crude product has a brown color and is slightly tacky. For purification, it is vigorously stirred in n-hexane for 12 hours. After removal of the supernatant hexane solution, ligand Ig is obtained as a white powder.

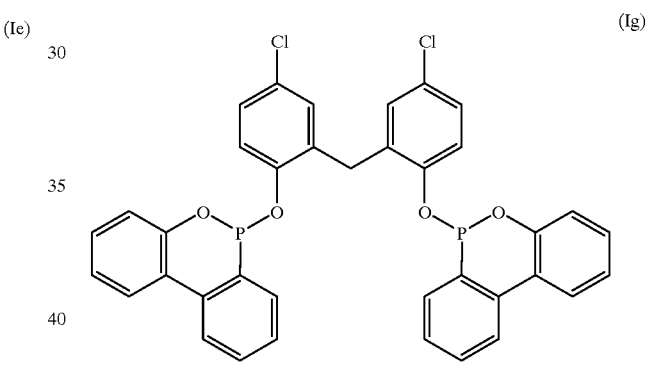

(Ig)

$^{31}$P-NMR spectrum: δ (ppm) 128.41

$^{1}$H-NMR spectrum: consistent with the proposed structure

Purity of crude product: >89%

B) Hydrocyanations and isomerizations

Example 8

(According to the Invention)

Semicontinuous hydrocyanation of $C_4$ cut using ligand Ia

TABLE 1

| Composition of the $C_4$ cut | |
|---|---|
| Compound | % by vol. |
| 1,3-butadiene | 40.50 |
| cis-2-butene | 2.65 |
| trans-2-butene | 4.30 |
| isobutene | 30.20 |
| 1-butene | 14.30 |
| isobutane | 1.10 |
| n-butane | 2.90 |

TABLE 1-continued

Composition of the C₄ cut

| Compound | % by vol. |
|---|---|
| propyne | 0.50 |
| carbon dioxide | 0.10 |
| vinylacetylene | 0.35 |

0.41 g (1.5 mmol) of bis(1,5-cyclooctadiene)nickel(0), 1.75 g (6 mmol) of ligand Ia and 6 g of toluene are mixed together in a glass autoclave at room temperature under argon, the mixture immediately becoming yellowish-brown. After about one hour, a mixture of 20 g of $C_4$ cut with a composition shown in Table 1 and 40 g of toluene is added. The glass autoclave is closed tightly and the mixture is heated to 80° C., setting up an initial pressure of 3.5 bar. A mixture of 4.0 g (0.15 mol) of freshly distilled hydrocyanic acid in 40 g of toluene is metered in continuously over the course of 120 minutes. The pressure has fallen to 2.9 bar after this. The reaction is then completed by further reaction at about 80° C. for 240 minutes; Toluene is used for washing the discharge from the reaction. The progress of the reaction is followed by measuring the pressure and temperature.

A subsequent Volhard cyanide determination shows that the hydrogen cyanide conversion was 86.7%.

GC analysis (column: 30 m stable wax, temperature program: 5 minutes isothermal at 50° C., then heating at a rate of 5° C./min to 240° C., gas chromatograph: Hewlett Packard HP 5890) with internal standard (benzonitrile): 84.0% 3-pentenonitrile, 4-pentenonitrile and 2-methyl-3-butenonitrile based on hydrogen cyanide.

3-Pentenonitrile:2-methyl-3-butenonitrile ratio=2.45:1.

Example 9

(According to the Invention)

Batch hydrocyanation of 1,3-butadiene using ligand Ia 0.10 g (0.37 mmol) of bis(1,5-cyclooctadiene)nickel(0), 0.43 g (1.48 mmol) of ligand Ia and 6.0 g of toluene are introduced into a stirred microvessel under argon and stirred at room temperature for 120 minutes. After addition of 2.0 g (37 mmol) of 1,3-butadiene and 1.0 g (37 mmol) of freshly distilled hydrocyanic acid, the vessel is closed with a tightly fitting septum and heated at 80° C. under autogenous pressure for 5 hours. After cooling, the liquid discharge from the reaction is analyzed.

TABLE 2

Product ratio in GC % areas

| Compound | GC % areas |
|---|---|
| trans-3-penteno-nitrile | 42.32 |
| 4-pentenonitrile | 0.33 |
| cis-3-pentenonitrile | 0.63 |
| 2-methyl-3-buteno-nitrile | 18.20 |

Yield (GC, internal standard benzonitrile): 93% 3-pentenonitrile, 4-pentenonitrile and 2-methyl-3-butenonitrile based on hydrogen cyanide.

3-Pentenonitrile:2-methyl-3-butenonitrile ratio=2.36:1.

Example 10

(According to the Invention)

Batch hydrocyanation of styrene with ligand Ia 6.0 g of toluene, 0.10 g (0.37 mmol) of bis(1,5-cyclooctadiene)nickel(O) and 0.43 g (1.48 mmol) of ligand Ia are introduced into a stirred microvessel under argon and stirred at room temperature for 120 minutes. After addition of 1.92 g (18.5 mmol) of styrene and 0.5 g (18.5 mmol) of freshly distilled hydrocyanic acid, the vessel is closed with a tightly fitting septum and kept at 120° C. (autogenous pressure) for 5 hours. After cooling, the liquid discharge from the reaction is analyzed. The gas chromatogram shows 2-phenylpropionitrile (12.53% area) and 3-phenylpropionitrile (0.16% area) and unreacted styrene (57.9% area).

Example 11

(According to the Invention)

Semicontinuous hydrocyanation of 3-pentenonitrile with ligand Ia 0.87 g (3 mmol) of ligand Ia, 20 ml of toluene and 0.27 g (1 mmol) of bis(1,5-cyclooctadiene)nickel(0) are mixed under an argon atmosphere and stirred at room temperature for 30 minutes. After addition of 16.2 g (200 mmol) of 3-pentenonitrile and 0.14 g (1 mmol) of $ZnCl_2$, the mixture is heated to 65° C. 5.4 g (200 mmol) of distilled HCN are passed in through a calibrated rotary evaporator in a stream of argon over the course of one hour. After subsequent reaction at 70° C. for one hour, the liquid discharge from the reaction is analyzed. It contains 2.87 GC % area adiponitrile, 0.72 GC % area methylglutaronitrile and 78.5 GC % area unreacted 3-pentenonitrile.

Example 12

(According to the Invention)

Isomerization of 2-methyl-3-butenonitrile to 3-pentenonitrile with ligand Ia 1.2 g (4 mmol) of ligand Ia, 10 ml of toluene and 0.275 g (1 mmol) of bis(1,5-cyclooctadiene)nickel(0) are mixed under an argon atmosphere and stirred at room temperature for 30 minutes. After addition of 8.1 g (100 mmol) of 2-methyl-3-butenonitrile and 0.55 g (4 mmol) of $ZnCl_2$, the mixture is heated to 100° C. The course of the reaction is investigated at regular intervals using a gas chromatograph. The result of the reaction is indicated in Table 3. All the products and byproducts listed there had previously been assigned by means of gas chromatography, GC-MS, GC-MS-IR and NMR. All the figures, except for 3-pentenonitrile and 2-methyl-3-butenonitrile, are GC % areas. With the latter, the GC % areas were converted into % by weight with the aid of calibration measurements.

TABLE 3

Product ratio after reaction for 300 minutes

| | Compound | Proportion |
|---|---|---|
| GC % areas | trans-2-methyl-2-butenonitrile | 2.76 |
| | 2-methyl-3-butenonitrile | 2.75 |
| | trans-2-pentenonitrile | 0.08 |
| | cis-2-methyl-2-butenonitrile | 1.56 |
| | 4-pentenonitrile | 0.98 |
| | trans-3-pentenonitrile | 29.68 |
| | cis-3-pentenonitrile | 1.74 |
| | benzonitrile (standard) | 52.34 |
| % by weight | 2-methyl-3-butenonitrile | 3.33 |
| | 3-pentenonitrile | 39.19 |

Conversion: 93.16%

Example 13

Preparation of a nickel(0) complex from elemental nickel

A phosphonite-nickel(0) complex is prepared starting from ligand Ia and elemental nickel powder. 14.6 g (50 mmol) of ligand Ia, 0.7 g (12.5 mmol) of nickel powder and 4.7 g of 3-pentenonitrile are mixed under an argon atmosphere and heated to 80° C. After addition of 2 drops of $PCl_3$, the mixture is stirred at 80° C. for 22 hours. The reddish brown viscous discharge from the reaction is, after cooling, filtered off with suction through a glass funnel. The average determined by elemental analysis of the homogeneous solution is 3.3% by weight (theory: 4.78% by weight), corresponding to a yield of 69% based on nickel powder.

Example 14

(According to the Invention)

Semicontinuous hydrocyanation of partially hydrogenated $C_4$ Cut

TABLE 4

Composition of the $C_4$ cut

| Compound | % by vol. |
| --- | --- |
| 1,3-butadiene | 38.90 |
| cis-2-butene | 4.30 |
| trans-2-butene | 7.05 |
| isobutene | 22.40 |
| 1-butene | 19.80 |
| isobutane | 0.89 |
| n-butane | 4.50 |
| propyne | 29 ppm |
| vinylacetylene | 159 ppm |
| 1-butyne | 187 ppm |

0.41 g (1.5 mmol) of bis(1,5-cyclooctadiene)nickel(0), 2.36 g (6 mmol) of ligand Ib and 6 g of toluene are mixed together in a glass autoclave at room temperature under argon. After about one hour, a mixture of 20.8 g of $C_4$ cut with a composition shown in Table 4 and 40 g of toluene is added. The glass autoclave is closed tightly and the mixture is heated to 80° C., setting up an initial pressure of 3.2 bar. A mixture of 4.0 g (0.15 mol) of freshly distilled hydrocyanic acid in 40 g of toluene is metered in continuously over the course of 120 minutes. The pressure has fallen to 2.3 bar after this. The reaction is then completed by further reaction at about 80° C. for 100 minutes. Toluene is used for washing the discharge from the reaction. The progress of the reaction is followed by measuring the pressure and temperature.

A subsequent Volhard cyanide determination shows that the hydrogen cyanide conversion was 65.3%.

GC analysis (column: 30 m stable wax, temperature program: 5 minutes isothermal at 50° C., then heating at a rate of 5° C./min to 240° C., gas chromatograph: Hewlett Packard HP 5890) with internal standard (benzonitrile): 64.7% 3-pentenonitrile, 4-pentenonitrile and 2-methyl-3-butenonitrile based on hydrogen cyanide.

3-Pentenonitrile:2-methyl-3-butenonitrile ratio=2.04:1.

Example 15

(According to the Invention)

Batch hydrocyanation of 1,3-butadiene using ligand Ib 0.10 g (0.37 mmol) of bis(1,5-cyclooctadiene)nickel(0), 0.56 g (1.48 mmol) of ligand Ib and 6.0 g of toluene are introduced into a stirred microvessel under argon and stirred at room temperature for 120 minutes. After addition of 2.0 g (37 mmol) of 1,3-butadiene and 1.0 g (37 mmol) of freshly distilled hydrocyanic acid, the vessel is closed with a tightly fitting septum and heated at 80° C. under autogenous pressure for 5 hours. After cooling, the liquid discharge from the reaction is analyzed.

TABLE 5

Product ratio in GC % areas

| Compound | GC % areas |
| --- | --- |
| trans-3-pentenonitrile | 40.82 |
| cis-3-pentenonitrile | 0.46 |
| 4-pentenonitrile | 0.22 |
| cis-2-methyl-butenonitrile | 0.08 |
| 2-methyl-3-butenonitrile | 19.64 |

Yield (GC, internal standard benzonitrile): 89.2% 3-pentenonitrile, 4-pentenonitrile and 2-methyl-3-butenonitrile based on hydrogen cyanide.

3-Pentenonitrile:2-methyl-3-butenonitrile ratio=2.1:1.

Example 16

(According to the Invention)

Semicontinuous hydrocyanation of 3-pentenonitrile using ligand Ib 1.13 g (3 mmol) of ligand Ib, 20 ml of toluene and 0.27 g (1 mmol) of bis(1,5-cyclooctadiene)nickel(0) are mixed under an argon atmosphere and stirred at room temperature for 30 minutes. After addition of 16.2 g (200 mmol) of 3-pentenonitrile and 0.14 g (1 mmol) of $ZnCl_2$, the mixture is heated to 65° C. 5.4 g (200 mmol) of freshly distilled hydrocyanic acid are passed in through a calibrated rotary evaporator in a stream of argon over the course of 90 minutes. After subsequent reaction at 75° C. for 90 minutes, the liquid discharge from the reaction is analyzed. It contains 2.98 GC % area adiponitrile, 0.67 GC % area methylglutaronitrile and 76.3 GC % area unreacted 3-pentenonitrile.

Example 17

(According to the Invention)

Isomerization of 2-methyl-3-butenonitrile to 3-pentenonitrile using ligand Ib 1.5 g (4 mmol) of ligand Ib, 10 ml of toluene and 0.275 g (1 mmol) of bis(1,5-cyclooctadiene)nickel(0) are mixed under an argon atmosphere and stirred at room temperature for 30 minutes. After addition of 8.1 g (100 mol) of 2-methyl-2-butenonitrile and 0.55 g of $ZuCl_2$, the mixture is heated to 100° C. Evaluation of reaction takes place as in Example 12. The result is shown in Table 6 which follows.

TABLE 6

Product ratio after reaction for 300 minutes

| | Compound | Proportion |
| --- | --- | --- |
| GC % areas | trans-2-methyl-2-butenonitrile | 7.69 |
| | 2-methyl-3-butenonitrile | 3.87 |
| | trans-2-pentenonitrile | 1.96 |
| | cis-2-methyl-2-butenonitrile | 15.06 |
| | 4-pentenonitrile | 0.07 |
| | trans-3-pentenonitrile | 16.82 |
| | cis-3-pentenonitrile | 0.40 |

TABLE 6-continued

Product ratio after reaction for 300 minutes

| | Compound | Proportion |
|---|---|---|
| % by weight | benzonitrile (standard) | 51.93 |
| | 2-methyl-3-butenonitrile | 4.09 |
| | 3-pentenonitrile | 18.20 |

Conversion: 90.58%

Example 18

(According to the Invention)

Batch hydrocyanation of 1,3-butadiene using ligand Ic 0.10 g (0.37 mmol) of bis(1,5-cyclooctadiene)nickel(0), 0.57 g (1.48 mmol) of ligand Ic and 6.0 g of toluene are introduced into a stirred microvessel under argon and stirred at room temperature for 120 minutes. After addition of 2.0 g (37 mmol) of 1,3-butadiene and 1.0 g (37 mmol) of freshly distilled hydrocyanic acid, the vessel is closed with a tightly fitting septum and heated at 80° C. under autogenous pressure for 5 hours. After cooling, the liquid discharge from the reaction is analyzed by gas chromatography. The result is shown in Table 7 which follows.

TABLE 7

Compound and GC % areas

| Compound | % by volume |
|---|---|
| trans-3-penteno-nitrile | 18.29 |
| cis-3-pentenonitrile | 0.12 |
| cis-2-methyl-buteno-nitrile | 0.03 |
| 2-methyl-3-buteno-nitrile | 8.72 |

Yield (GC, internal standard benzonitrile): 35.1%

3-pentenonitrile, 4-pentenonitrile and 2-methyl-3-butenonitrile based on hydrogen cyanide.

3-Pentenonitrile:2-methyl-3-butenonitrile ratio=2.11:1.

Example 19

(According to the Invention)

Semicontinuous hydrocyanation of 1,3-butadiene using ligand Ic 0.41 g (1.5 mmol) of bis(1,5-cyclooctadiene)nickel(0), 2.03 g (6 mmol) of ligand Ic and 6 g of toluene are mixed together in a glass autoclave at room temperature under argon. After about 1 hour, a mixture of 8.1 g of 1,3-butadiene in 40 g of toluene is added. The glass autoclave is closed tightly and the mixture is heated to 110° C., setting up an initial pressure of 2.0 bar. A mixture of 4.0 g (0.15 mol) of freshly distilled hydrocyanic acid in 40 g of toluene is metered in continuously over the course of 120 minutes. The pressure has fallen to 1.5 bar after this. The reaction is then completed by further reaction at about 110° C. for 310 minutes. Toluene is used for washing the discharge from the reaction. The progress of the reaction is followed by measuring the pressure and temperature. A subsequent Volhard cyanide determination shows that the hydrogen cyanide conversion was 74.3%.

GC analysis (column: 30 m stable wax, temperature program: 5 minutes isothermal at 50° C., then heating at a rate of 5° C./min to 240° C., gas chromatograph: Hewlett Packard HP 5890) with internal standard (benzonitrile): 72.5%

3-pentenonitrile, 4-pentenonitrile and 2-methyl-3-butenonitrile based on hydrogen cyanide.

3-Pentenonitrile:2-methyl-3-butenonitrile ratio=1.89:1.

Example 20

(According to the Invention)

Semicontinuous hydrocyanation of 3-pentenonitrile using ligand Ic 1.15 g (3 mmol) of ligand Ic, 20 ml of toluene and 0.27 g (1 mmol) of bis(1,5-cyclooctadiene)nickel(0) are mixed under an argon atmosphere and stirred at room temperature for 30 minutes. After addition of 24.3 g (300 mmol) of 3-pentenonitrile and 0.14 g (1 mmol) of $ZnCl_2$, the mixture is heated to 60° C. 5.4 g (200 mmol) of distilled hydrocyanic acid are passed in through a calibrated rotary evaporator in a stream of argon over the course of 2 hours. After subsequent reaction at 70° C. for 1 hour, the liquid discharge from the reaction is analyzed. It contains 1.66 GC % area adiponitrile, 0.34 GC % area methylglutaronitrile and 82.3 GC % area unreacted 3-pentenonitrile.

Example 21

(According to the Invention)

Batch hydrocyanation of 1,3-butadiene using ligand Id 0.10 g (0.37 mmol) of bis(1,5-cyclooctadiene)nickel(0), 0.46 g (1.48 mmol) of ligand Id and 6.0 g of toluene are introduced into a stirred microvessel under argon and stirred at room temperature for 120 minutes. After addition of 2.0 g (37 mmol) of 1,3-butadiene and 1.0 g (37 mmol) of freshly distilled hydrocyanic acid, the vessel is closed with a tightly fitting septum and heated at 80° C. under autogenous pressure for 5 hours. After cooling, the liquid discharge from the reaction is analyzed.

Yield (GC, internal standard benzonitrile): 8.9%

3-pentenonitrile, 4-pentenonitrile and 2-methyl-3-butenonitrile based on hydrogen cyanide.

3-Pentenonitrile:2-methyl-3-butenonitrile ratio=2.1:1.

Example 22

(According to the Invention)

Semicontinuous hydrocyanation of 3-pentenonitrile with ligand Id 0.93 g (3 mmol) of ligand Id, 20 ml of toluene and 0.27 g (1 mmol) of bis(1,5-cyclooctadiene)nickel(0) are mixed under an argon atmosphere and stirred at room temperature for 30 minutes. After addition of 16.2 g (200 mmol) of 3-pentenonitrile and 0.14 g (1 mmol) of $ZnCl_2$, the mixture is heated to 60° C. 5.4 g (200 mmol) of distilled hydrocyanic acid are passed in through a calibrated rotary evaporator in a stream of argon over the course of 2 hours. After subsequent reaction at 70° C. for 1 hour, the liquid discharge from the reaction is analyzed. It contains 1.01 GC % area adiponitrile, 0.25 GC % area methylglutaronitrile and 84.99 GC % area unreacted 3-pentenonitrile.

Example 23

(According to the Invention)

Batch hydrocyanation of 1,3-butadiene using ligand Ie 0.10 g (0.37 mmol) of bis(1,5-cyclooctadiene)nickel(0), 0.62 g (1.8 mmol) of ligand Ie and 6.0 g of toluene are introduced into a stirred microvessel under argon and stirred at room temperature for 120 minutes. After addition of 2.0 g (37 mmol) of 1,3-butadiene and 1.0 g (37 mmol) of freshly distilled hydrocyanic acid, the vessel is closed with a tightly fitting septum and heated at 80° C. under autogenous pressure for 5 hours. After cooling, the liquid discharge from the reaction is analyzed.

Yield (GC, internal standard benzonitrile): 9.7%

3-pentenonitrile, 4-pentenonitrile and 2-methyl-3-butenonitrile based on hydrogen cyanide.

3-Pentenonitrile:2-methyl-3-butenonitrile ratio=1.94:1.

Example 24

(According to the Invention)

Semicontinuous hydrocyanation of 3-pentenonitrile using ligand Ie 1.26 g (3 mmol) of ligand Ie, 20 ml of toluene and 0.27 g (1 mmol) of bis(1,5-cyclooctadiene)nickel(0) are mixed under an argon atmosphere and stirred at room temperature for 30 minutes. After addition of 16.2 g (200 mmol) of 3-pentenonitrile and 0.14 g (1 mmol) of $ZnCl_2$, the mixture is heated to 60° C. 5.4 g (200 mmol) of distilled hydrocyanic acid are passed in through a calibrated rotary evaporator in a stream of argon over the course of 2 hours. After subsequent reaction at 70° C. for 1 hour, the liquid discharge from the reaction is analyzed. It contains 1.06 GC % area adiponitrile, 0.24 GC % area methylglutaronitrile and 83.7 GC % area unreacted 3-pentenonitrile.

We claim:

1. A catalyst comprising a nickel(0) complex having a mono-, bi- or multidentate phosphonite ligand of the formula I

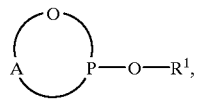
(I)

where
A is, together with the part of the phosphonite group to which it is bonded, a 5- to 8-membered heterocycle which may additionally be fused once, twice or three times to cycloalkyl, aryl and/or heteroaryl where the fused groups may in each case have one, two or three substituents selected from alkyl, alkoxy, halogen, nitro, cyano or carboxyl, $R^1$ is alkyl, aryl or heteroaryl, each of which may have one, two or three of the following substituents: alkyl, cycloalkyl, aryl, alkoxy, cycloalkyloxy, acyl, aryloxy, halogen, trifluoromethyl, nitro, cyano, carboxyl or $NE^1E^2$ may be identical or different and are alkyl, cycloalkyl or aryl, or $R^1$ is a radical of the formula II

(II)

where
X is a $C_3$–$C_6$-alkylene bridge which may have one, two or three double bonds and/or be fused once, twice or three times with aryl and/or heteroaryl, where the aryl or heteroaryl groups may have one, two or three of the following substituents: alkyl, cycloalkyl, aryl, alkoxy, cycloalkyloxy, aryloxy, halogen, trifluoromethyl, nitro, cyano, carboxyl or $NE^1N^2$, where $E^1$ and $E^2$ have the abovementioned meanings, Y is a radical of the formula III.1 or III.2

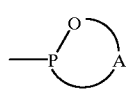
(III.1)

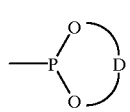
(III.2)

where
D can have the meanings stated previously for A, or salt and mixture thereof.

2. A catalyst as claimed in claim 1, where A is, together with the part of the phosphonite group to which it is bonded, a 5- or 6-membered heterocycle which may be fused once or twice to aryl and/or hetaryl, where the fused groups may have one, two or three of the above mentioned substituents.

3. A catalyst as claimed in claim 1, where A is a radical of the formula IV.1 or IV.2 or IV.3

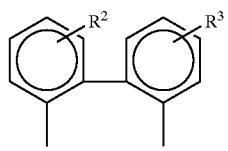
(IV.1)

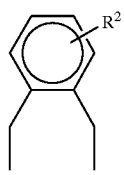
(IV.2)

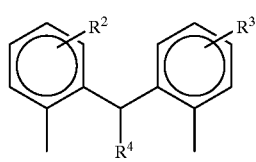
(IV.3)

where
$R^2$ and $R^3$ are, independently of one another, hydrogen, alkyl, alkoxy, halogen, trifluoromethyl, nitro or cyano, $R^4$ is hydrogen, alkyl, or aryl, which may be substituted by alkyl, alkoxy, halogen, trifluoromethyl, nitro or cyano.

4. A catalyst as claimed in claim 1, where
$R^1$ is a phenyl or naphthyl, which may have one, two or three of the following substituents: alkyl, alkoxy, halogen, nitro, cyano, carboxyl or $NE^1E^2$, where $E^1$ and $E^2$ have the above mentioned meanings, or $R^1$ is a radical of the formula II where
X is a $C_4$–$C_5$-alkylene bridge which may have one or two double bonds and/or be fused once or twice to aryl and/or hetaryl, where the aryl or hetaryl groups may have one, two or three of the following substituents: alkyl, cycloalkyl, aryl, alkoxy, cycloalkyloxy, aryloxy, halogen, nitro, cyano, carboxyl or $NE^1E^2$, where $E^1$ and $E^2$ have the abovementioned meanings, and Y is a radical of the formula III.1 or III.2, where D is a radical of the formula IV.1, IV.2 or IV.3

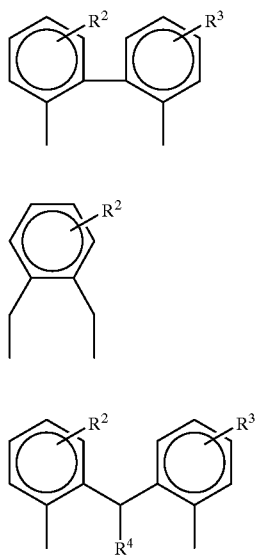

(IV.1)

(IV.2)

(IV.3)

where

R² and R³ are, independently of one another, hydrogen, alkyl, alkoxy, halogen, trifluoromethyl, nitro or cyano, R⁴ is hydrogen, alkyl, or aryl, which may be substituted by alkyl, alkoxy, halogen, trifluoromethyl, nitro or cyano.

5. A catalyst as claimed in claim 1, where in formula I, $R^1$ is a radical of the formula II where X is formulae X.1 to X.5

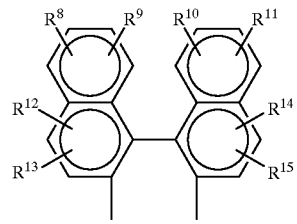

(X.1)

(X.2)

(X.3)

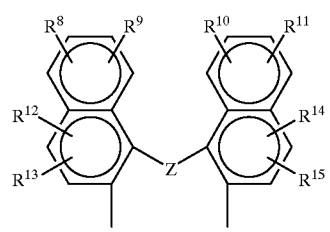

(X.4)

(X.5)

wherein

Z is O, S, NR¹⁶ or CHR¹⁷, wherein

R¹⁶ is alkyl, cycloalkyl or aryl, and

R¹⁷ is hydrogen, alkyl, cycloalkyl or aryl, where the aryl substituent may have one, two or three of the following substituents: alkyl, alkoxy, halogen, trifluoromethyl, nitro, alkoxycarbonyl or cyano, R⁸, R⁹, R¹⁰, R¹¹, R¹², R¹³, R¹⁴ and R¹⁵ are, independently of one another, hydrogen, alkyl, alkoxy, halogen, trifluoromethyl, nitro, alkoxycarbonyl or cyano.

6. A catalyst as claimed in claim 1, where the phosphonite ligand of the formula I is selected from formulae Ia to Ih

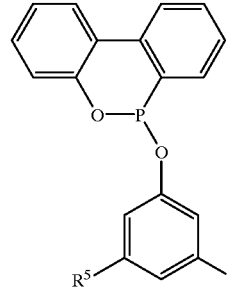

(Ia)

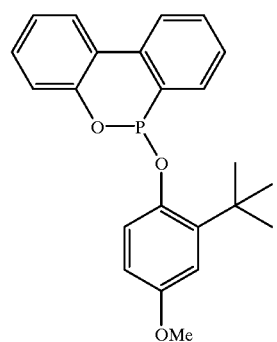

(Ib)

(Ic)
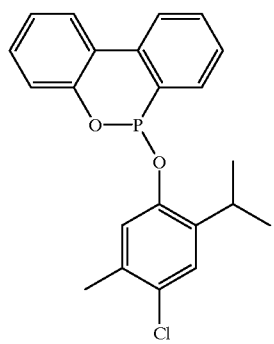
(Id)
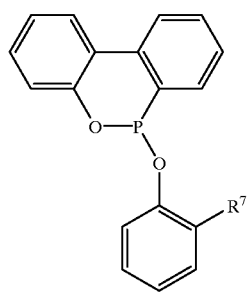
(Ie)
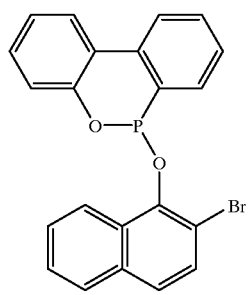
(If)
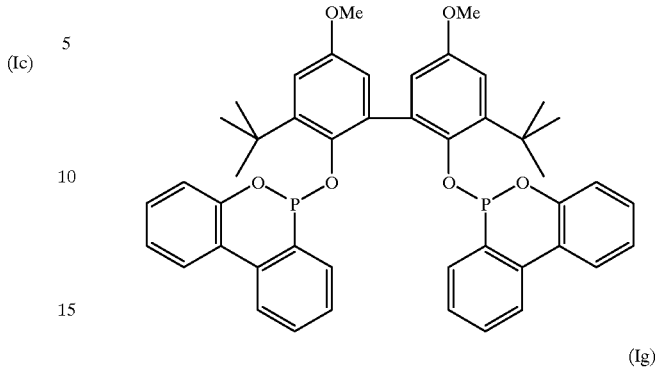
(Ig)
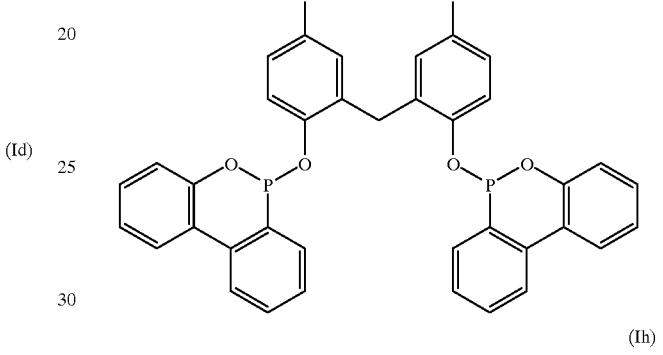
(Ih)
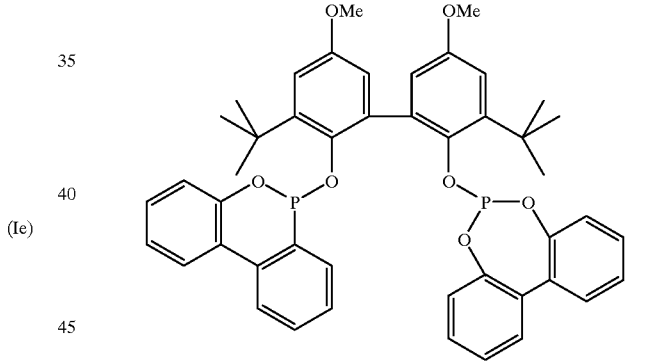
where
R[5] and R[6], independently of one another, are hydrogen or trifluoromethyl,
R[7] is fluorine or trifluoromethyl.
* * * * *

UNITED STATES PATENT AND TRADEMARK OFFICE
CERTIFICATE OF CORRECTION

PATENT NO. : 6,355,833 B2
DATED : March 12, 2002
INVENTOR(S) : Fischer et al.

It is certified that error appears in the above-identified patent and that said Letters Patent is hereby corrected as shown below:

<u>Column 25,</u>
Line 54, after "$NE^1E^2$" insert -- where $E^1$ and $E^2$ --.

Signed and Sealed this

First Day of October, 2002

Attest:

Attesting Officer

JAMES E. ROGAN
*Director of the United States Patent and Trademark Office*